United States Patent
Cheng et al.

(10) Patent No.: US 11,441,168 B2
(45) Date of Patent: Sep. 13, 2022

(54) METHOD FOR ASSAYING THE ACTIVITY OF SPERMIDINE/SPERMINE $N^1$-ACETYLTRANSFERASE

(71) Applicant: BioMark Technologies Inc., Richmond (CA)

(72) Inventors: Brian Cheng, Richmond (CA); Rashid Bux, Richmond (CA); Daniel Sitar, Richmond (CA)

(73) Assignee: BioMark Technologies Inc., Richmond (CA)

( * ) Notice: Subject to any disclaimer, the term of this patent is extended or adjusted under 35 U.S.C. 154(b) by 0 days.

(21) Appl. No.: 17/406,956

(22) Filed: Aug. 19, 2021

(65) Prior Publication Data

US 2022/0033875 A1    Feb. 3, 2022

Related U.S. Application Data

(63) Continuation of application No. 14/358,695, filed as application No. PCT/CA2012/050828 on Nov. 16, 2012, now abandoned.

(60) Provisional application No. 61/560,700, filed on Nov. 16, 2011.

(51) Int. Cl.
*C12Q 1/48* (2006.01)
*G01N 33/574* (2006.01)

(52) U.S. Cl.
CPC ......... *C12Q 1/48* (2013.01); *G01N 33/57407* (2013.01)

(58) Field of Classification Search
None
See application file for complete search history.

(56) References Cited

U.S. PATENT DOCUMENTS 6,811,967 B2    11/2004   Sitar et al.

FOREIGN PATENT DOCUMENTS

WO    WO2002/070732 A2    9/2002

OTHER PUBLICATIONS

Govorkova et al., Antimicrob. Agents Chemother. 48(12): 4855-4863 (2004).*
Govorkova, E.A. et al., "Neuraminidase Inhibitor-Rimantadine Combinations Exert Additive and Synergistic Anti-Influenza Virus Effects in MDCK Cells," *Antimicrobial Agents and Chemotherapy*, Vo. 48, No. 12, Dec. 17, 2004, pp. 4855-4863, 9 pages.
European Patent Office, Examination Report dated Jun. 6, 2018 in European Patent Application No. 12850541.9, 3 pages.
European Patent Office, Examination Report dated Jun. 7, 2016 in European Patent Application No. 12850541.9, 4 pages.
European Patent Office, Extended Search Report dated May 19, 2015 in European Patent Application No. 12850541.9, 5 pages.

(Continued)

*Primary Examiner* — Erin M. Bowers
(74) *Attorney, Agent, or Firm* — Hovey Williams LLP

(57) ABSTRACT

A method for assaying activity of the enzyme spermidine/spermine $N^1$-acetyltransferase (SSAT) uses SSAT substrates by detecting their acetylated forms. SSAT substrates may include rimantadine and tocainide wherein their metabolism occurs in part by the action of the inducible enzyme SSAT to produce the acetylated metabolites N-acetylrimantadine and N-acetyltocainide respectively. SSAT activity may be correlated to pathologic conditions.

10 Claims, 22 Drawing Sheets

| SSAT Substrate | Km (µM) | Vmax (pmol/min/million cells) |
|---|---|---|
| Amantadine | 1659 | 0.00197 |
| Rimantadine | 1835 | 0.364 |
| Tocainide | 5033 | 0.617 |
| Spermidine | 287 | 7.21 |

Summary of Enzyme Kinetic Parameters

(56) References Cited

OTHER PUBLICATIONS

WIPO, Canadian International Search Authority, International Search Report dated Mar. 8, 2013 in International Patent Application No. PCT/CA2012/050828, 5 pages.

Pegg, A., "Spermidine/spermine TV1-acetyltransferase: a key metabolic regulator," *Am J Physiol Endocrinol Metab* 293: E995-E1010, Mar. 18, 2018, 16 pages.

Gerner, E.W. et al., "Polyamines and Cancer: Old Molecules, New Understanding," *Nature Review |Cancer*, vol. 4, Oct. 2004, pp. 781-792, 12 pages.

Wang, Z. et al., "Overexpression of SSAT in Kidney Cells Recapitulates Various Phenotypic Aspects of Kidney Ischemia-reperfusion Injury," *J Am Soc Hephrol*, 15:1844-1852, Jul. 2004, 9 pages.

Bras, A.P.M. et al., "Spermidine/SpermineN[1]-Acetyltransferase Catalyzes Amantadine Acetylation," *Drug Metabolism and Disposition*, May 1, 2001, 29(5) 676-680, Abstract, 2 pages.

Casero, Jr, R.A. et al., "Spermidine/spermine N[1]-acetyltransferase—the turning point in polyamine metabolism," *The FASEB Journal*, vol. 7, May 1, 1993, pp. 653-661, 9 pages.

\* cited by examiner

| SSAT Substrate | Km (µM) | Vmax (pmol/min/million cells) |
|---|---|---|
| Amantadine | 1659 | 0.00197 |
| Rimantadine | 1835 | 0.364 |
| Tocainide | 5033 | 0.617 |
| Spermidine | 287 | 7.21 |

Figure 1    Summary of Enzyme Kinetic Parameters

| Amantadine Substrate Conc (μM) | Metabolite Formation (pmol/min/million cells) | 1 / Amantadine Substrate Conc (μM) | 1 / Metabolite Formation (pmol/min/million cells) |
|---|---|---|---|
| 107[a] | 0.000172[a] | 0.00936[a] | 5828[a] |
| 160 | 0.000184 | 0.00624 | 5424 |
| 214 | 0.000202 | 0.00468 | 4943 |
| 267 | 0.000283 | 0.00375 | 3531 |
| 401 | 0.000343 | 0.00250 | 2919 |
| 534 | 0.000441 | 0.00187 | 2265 |
| 668 | 0.000629 | 0.00150 | 1590 |
| 801 | 0.000708 | 0.00125 | 1413 |
| 935 | 0.000755 | 0.00107 | 1324 |
| 1068 | 0.000795 | 0.000936 | 1258 |
| 1335[b] | 0.000979[b] | 0.000749[b] | 1022[b] |

[a] Data observed to be out of trend; excluded from analysis.
[b] Cytotoxicity observed; data excluded from analysis.

Figure 2    Enzyme Kinetic Data of Amantadine N-Acetylation by SSAT

| Rimantadine Substrate Conc (µM) | Metabolite Formation (pmol/min/million cells) | 1 / Rimantadine Substrate Conc (µM) | 1 / Metabolite Formation (pmol/min/million cells) |
|---|---|---|---|
| 20.0[a] | 0.00137[a] | 0.0500[a] | 731[a] |
| 40.0 | 0.00727 | 0.0250 | 138 |
| 60.0 | 0.0127 | 0.0167 | 79.0 |
| 80.0 | 0.0167 | 0.0125 | 59.8 |
| 100 | 0.0218 | 0.0100 | 46.0 |
| 120 | 0.0226 | 0.00833 | 44.2 |
| 150 | 0.0264 | 0.00667 | 37.9 |
| 180 | 0.0273 | 0.00556 | 36.6 |
| 200 | 0.0294 | 0.00500 | 34.0 |
| 250[b] | 0.0382[b] | 0.00400[b] | 26.2[b] |
| 300[b] | 0.0496[b] | 0.00333[b] | 20.2[b] |

[a] < LLOQ; data excluded from analysis.
[b] Cytotoxicity observed; data excluded from analysis.

Figure 3   Enzyme Kinetic Data of Rimantadine N-Acetylation by SSAT

| Tocainide Substrate Conc (µM) | Metabolite Formation (pmol/min/million cells) | 1 / Tocainide Substrate Conc (µM) | 1 / Metabolite Formation (pmol/min/million cells) |
|---|---|---|---|
| 20.0[a] | 0.000897[a] | 0.0500[a] | 1115[a] |
| 40.0[a] | 0.00368[a] | 0.0250[a] | 272[a] |
| 60.0 | 0.00690 | 0.0167 | 145 |
| 80.0 | 0.0105 | 0.0125 | 94.9 |
| 100 | 0.0131 | 0.0100 | 76.4 |
| 150 | 0.0144 | 0.00667 | 69.3 |
| 200 | 0.0267 | 0.00500 | 37.5 |
| 300 | 0.0463 | 0.00333 | 21.6 |
| 400 | 0.0474 | 0.00250 | 21.1 |
| 500 | 0.0435 | 0.00200 | 23.0 |
| 600 | 0.0626 | 0.00167 | 16.0 |
| 800 | 0.0800 | 0.00125 | 12.5 |
| 1000 | 0.0919 | 0.00100 | 10.9 |

[a] < LLOQ; data excluded from analysis.

Figure 4  Enzyme Kinetic Data of Tocainide N-Acetylation by SSAT

| Spermidine Susbtrate Conc (μM) | Metabolite Formation (pmol/min/million cells) | 1 / Spermidine Susbtrate Conc (μM) | 1 / Metabolite Formation (pmol/min/million cells) |
|---|---|---|---|
| 11.0 | 0.256 | 0.0909 | 3.91 |
| 22.0 | 0.606 | 0.0455 | 1.65 |
| 33.0 | 0.756 | 0.0303 | 1.32 |
| 55.0 | 1.33 | 0.0182 | 0.749 |
| 110 | 1.31 | 0.00909 | 0.762 |
| 165 | 1.89 | 0.00606 | 0.530 |
| 220 | 2.82 | 0.00455 | 0.355 |
| 275 | 4.08 | 0.00364 | 0.245 |
| 330 | 4.39 | 0.00303 | 0.228 |
| 440 | 4.62 | 0.00227 | 0.217 |
| 550 | 7.19 | 0.00182 | 0.139 |

Figure 5    Enzyme Kinetic Data of Spermidine N-Acetylation by SSAT

| Amantadine Susbtrate Conc (µM) | Relative Viability % | Rimantadine Susbtrate Conc (µM) | Relative Viability % | Tocainide Susbtrate Conc (µM) | Relative Viability % |
|---|---|---|---|---|---|
| | Hepatocyte Lot SKN | | Hepatocyte Lot ASM | | Hepatocyte Lot ASM |
| 0.00 | 100.0 | 0.00 | 100.0 | 0.00 | 100.0 |
| 53.4 | 84.4 | 20.0 | 99.0 | 10.0 | 100.5 |
| 107 | 85.3 | 40.0 | 100.2 | 20.0 | 100.6 |
| 187 | 90.4 | 100 | 85.7 | 50.0 | 94.1 |
| 267 | 72.9 | 200 | 72.5 | 100 | 97.7 |
| 401 | 75.5 | 400 | 12.2 | 200 | 96.9 |
| 534 | 68.5 | 600 | 6.8 | 300 | 94.3 |
| 801 | 66.2 | 800 | 6.5 | 400 | 90.7 |
| 1068 | 58.1 | 1000 | 4.9 | 500 | 92.9 |
| 1602 | 14.8 | | Hepatocyte Lot SKN | | Hepatocyte Lot SKN |
| 2136 | 7.2 | 200 | 73.7 | 100 | 99.4 |
| 2670 | 9.7 | 1000 | 5.9 | 500 | 99.9 |

* The pilot experiment was performed with two lots of rat hepatocytes (Lots ASM and SKN). MTT assay results indicated comparable cell viability between the two lots when both lots were treated at the same concentrations of Rimantadine (200 µM and 1000 µM) and Tocainide (100 µM and 500 µM).

Figure 6    Results of MTT Assays from the Pilot Experiment

| Amantadine Susbtrate Conc (µM) | Relative Viability % | Rimantadine Susbtrate Conc (µM) | Relative Viability % | Tocainide Susbtrate Conc (µM) | Relative Viability % | Spermidine Susbtrate Conc (µM) | Relative Viability % |
|---|---|---|---|---|---|---|---|
| 0.00 | 100.0 | 0.00 | 100.0 | 0.00 | 100.0 | 0.00 | 100.0 |
| 106 | 92.9 | 20.0 | 93.3 | 20.0 | 101.2 | 11.0 | 97.2 |
| 160 | 96.8 | 40.0 | 84.8 | 40.0 | 105.4 | 22.0 | 97.5 |
| 213 | 93.2 | 60.0 | 81.0 | 60.0 | 106.4 | 33.0 | 98.4 |
| 267 | 87.0 | 80.0 | 78.1 | 80.0 | 105.1 | 55.0 | 99.0 |
| 401 | 80.3 | 100 | 71.1 | 100 | 97.1 | 110 | 87.5 |
| 534 | 71.7 | 120 | 69.7 | 150 | 102.3 | 165 | 89.5 |
| 668 | 74.0 | 150 | 64.3 | 200 | 96.5 | 220 | 86.5 |
| 801 | 66.5 | 180 | 65.1 | 300 | 108.2 | 275 | 85.5 |
| 934 | 62.0 | 200 | 59.2 | 400 | 93.7 | 330 | 94.6 |
| 1068 | 57.3 | 250 | 35.5 | 500 | 86.9 | 440 | 88.7 |
| 1335 | 31.8 | 300 | 14.5 | 600 | 78.2 | 550 | 86.3 |
|  |  |  |  | 800 | 89.0 |  |  |
|  |  |  |  | 1000 | 75.0 |  |  |

*The confirmatory experiment was only performed with rat hepatocyte lot SKN.

Figure 7  Results of MTT Assays from the Confirmatory Experiment

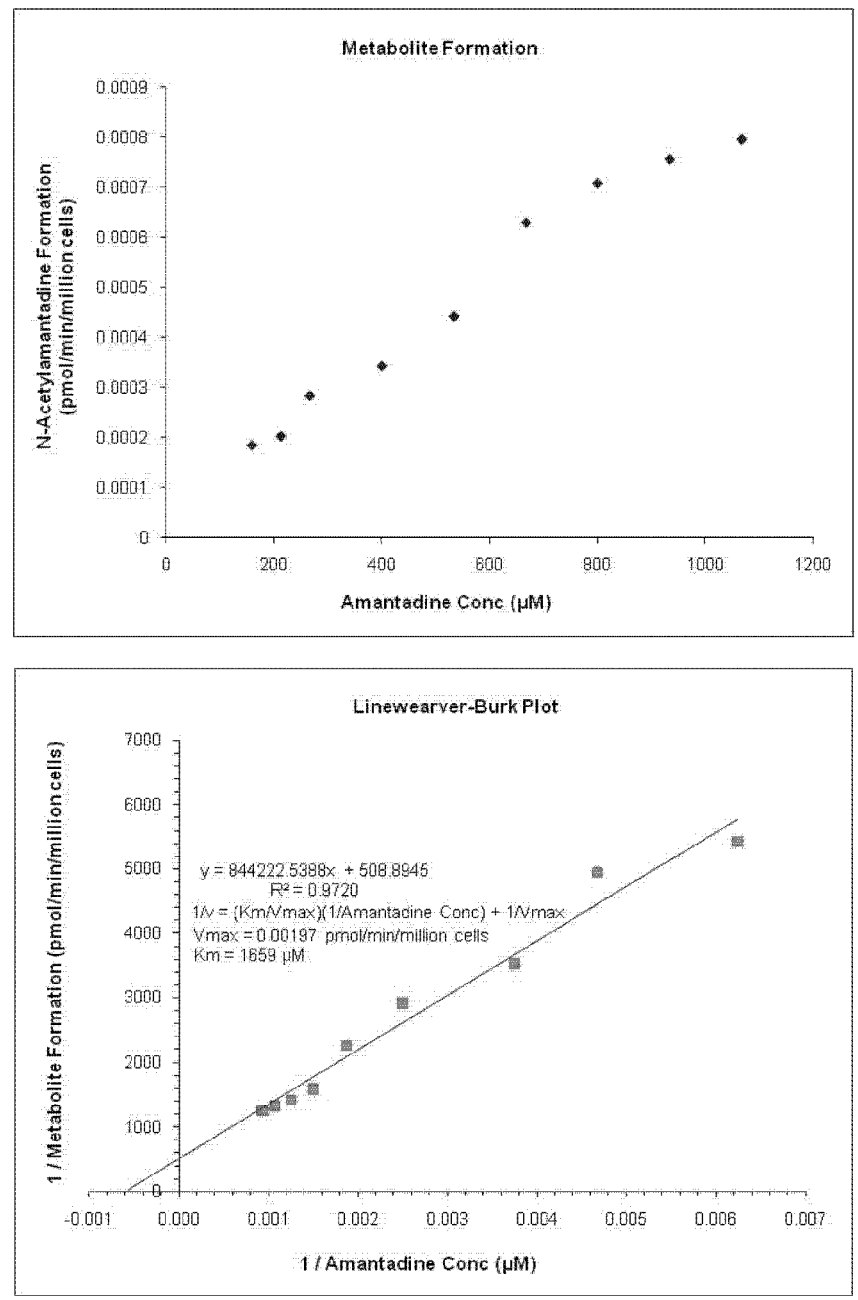
Figure 8   Metabolite Formation and Lineweaver-Burk Plot of N-Acetylation of Amantadine by SSAT Indicating Vmax = 0.00197 pmol/min/million cells and Km = 1659 µM

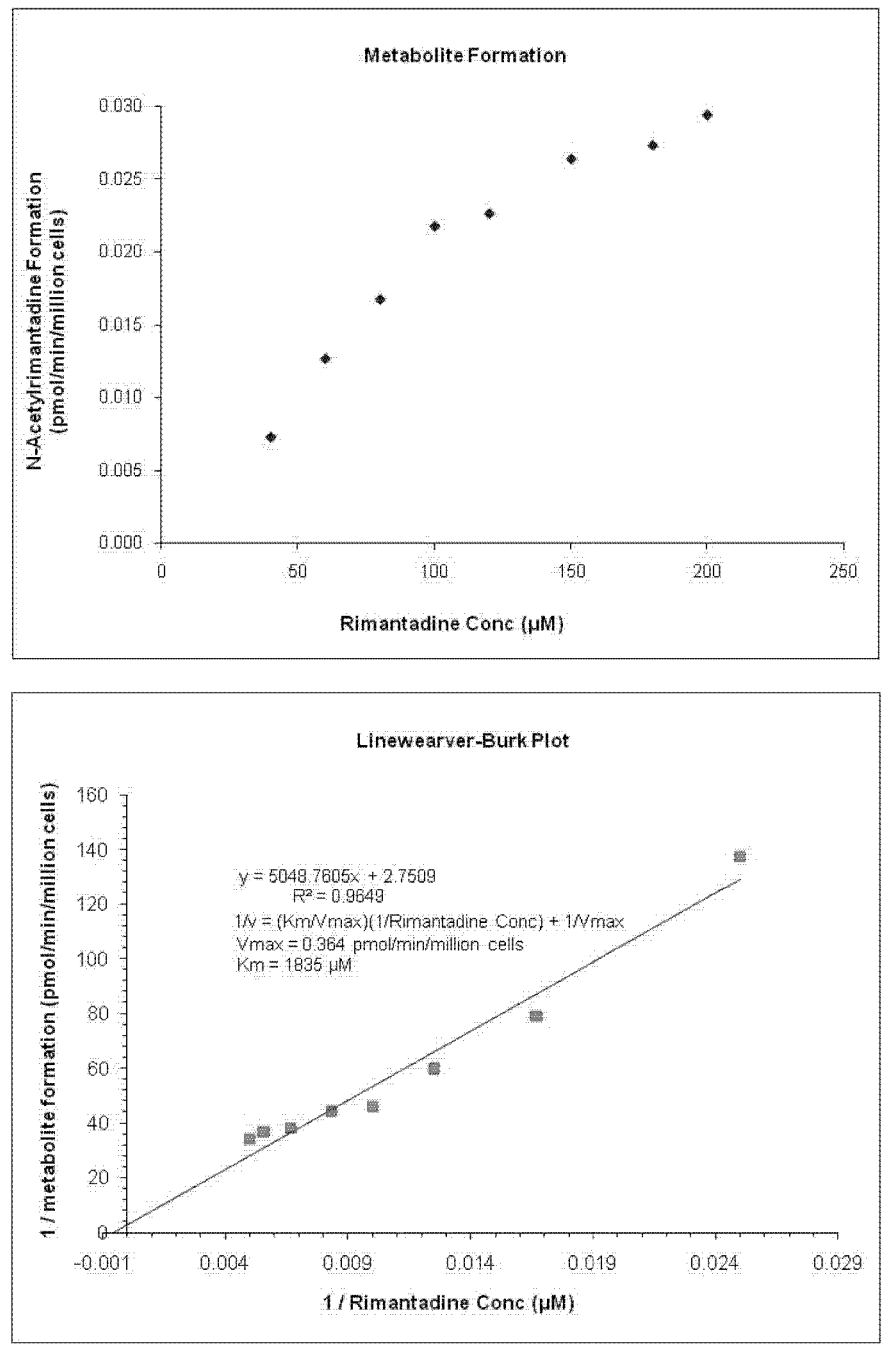
Figure 9  Metabolite Formation and Lineweaver-Burk Plot of N-Acetylation of Rimantadine by SSAT Indicating Vmax = 0.364 pmol/min/million cells and Km = 1835 μM

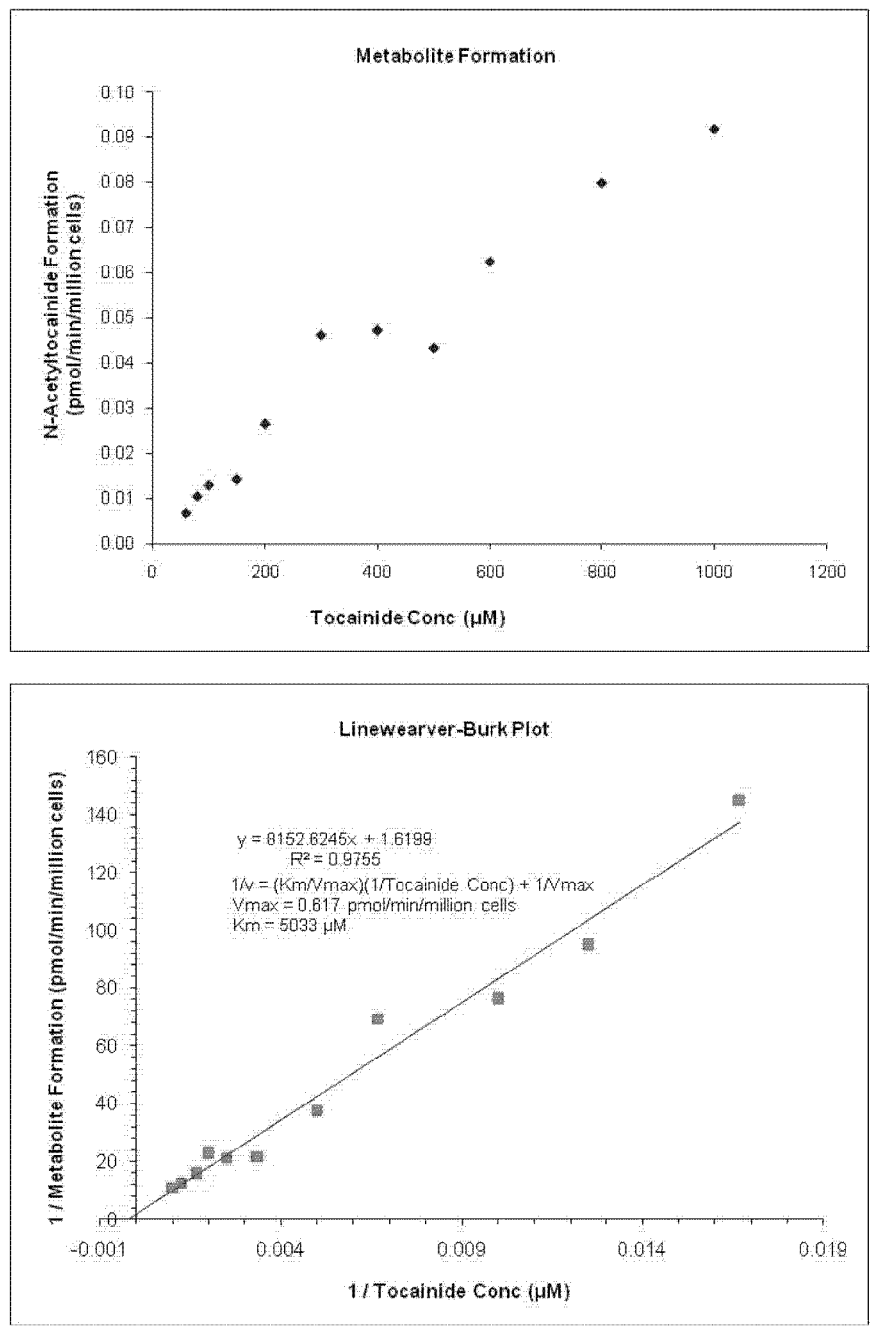
Figure 10  Metabolite Formation and Lineweaver-Burk Plot of N-Acetylation of Tocainide by SSAT Indicating Vmax = 0.617 pmol/min/million cells and Km = 5033 µM

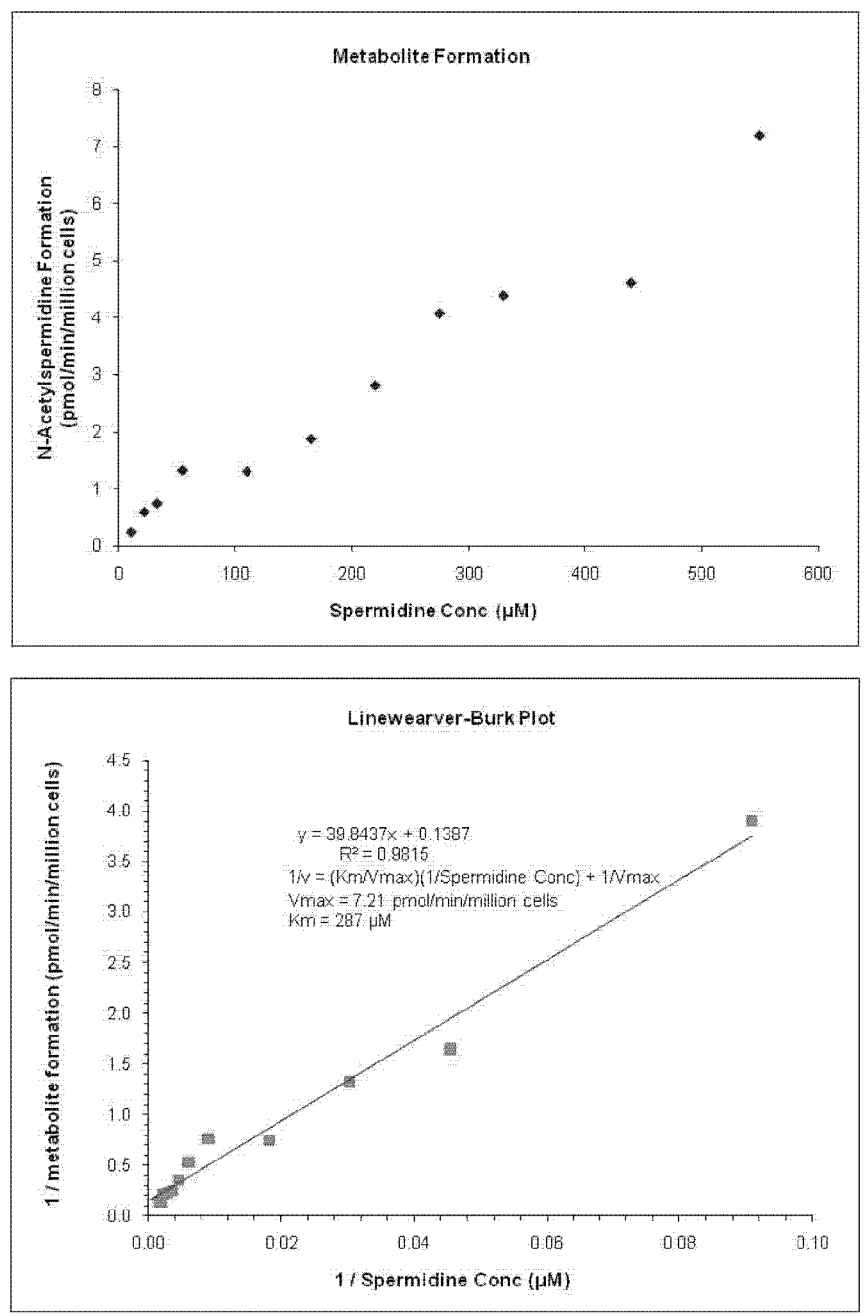
Figure 11 Metabolite Formation and Lineweaver-Burk Plot of N-Acetylation of Spermidine by SSAT Indicating Vmax = 7.21 pmol/min/million cells and Km = 287 μM

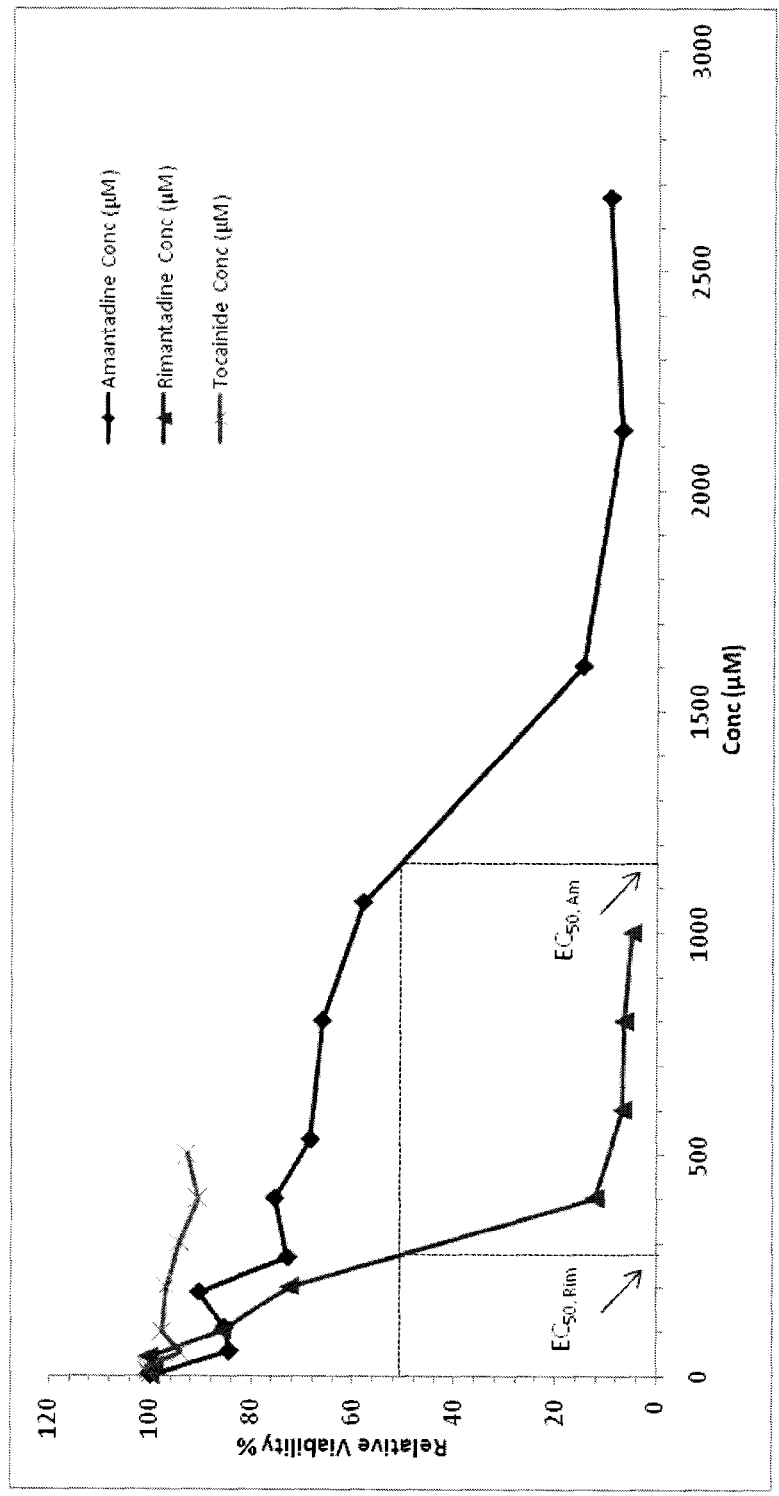
$EC_{50}$ = Concentration resulting in 50% relative viability; Am = Amantadine; Rim = Rimantadine
Figure 12   Results of MTT Assay from the Pilot Experiment Indicating Significant Cytotoxicity at Approximately 1170 µM of Amantadine and 280 µM of Rimantadine

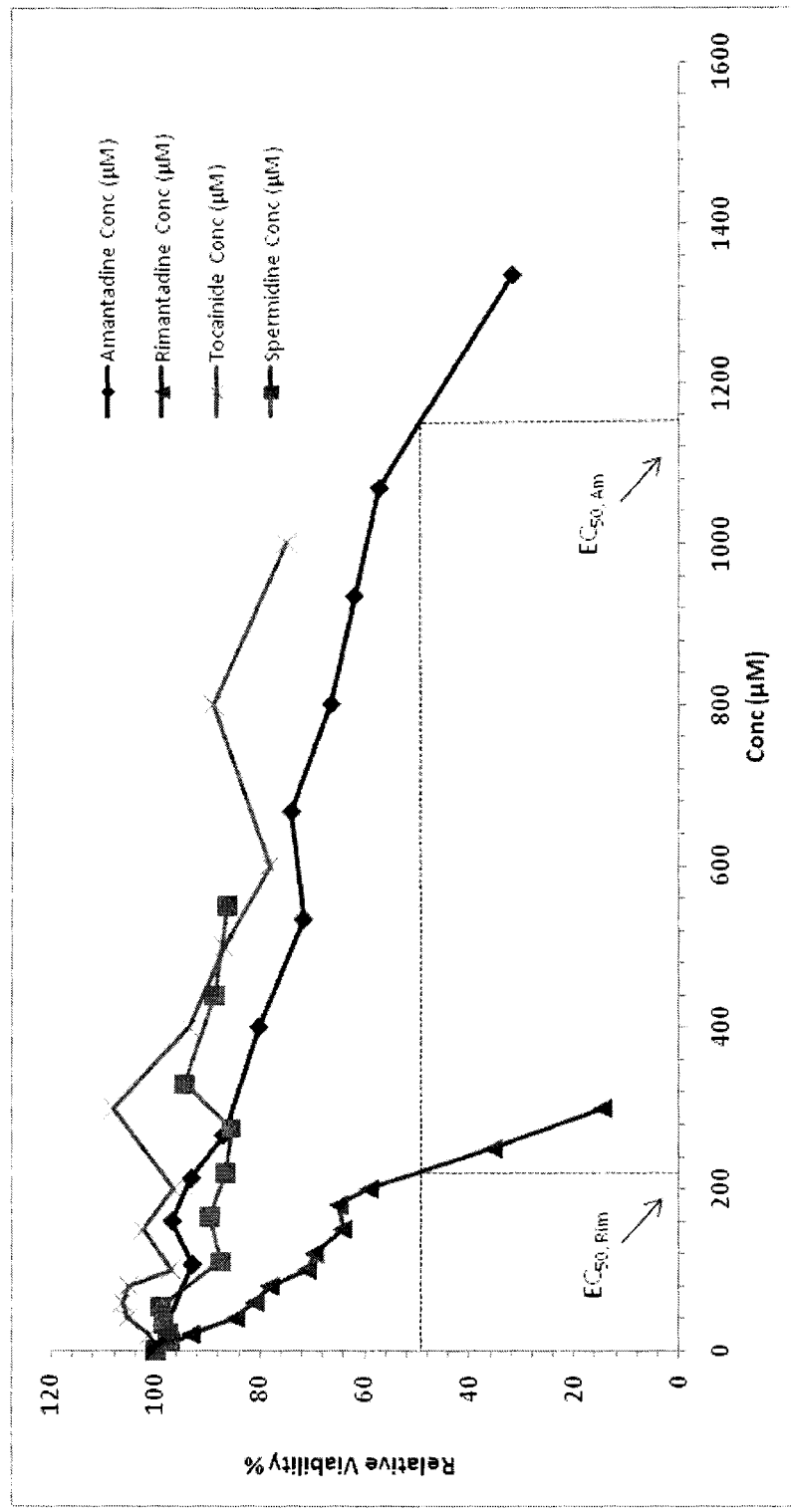
EC$_{50}$ = Concentration resulting in 50% relative viability; Am = Amantadine; Rim = Rimantadine
Figure 13    Results of MTT Assay from the Confirmatory Experiment Indicating Significant Cytotoxicity at Approximately 1140 µM of Amantadine and 220 µM of Rimantadine

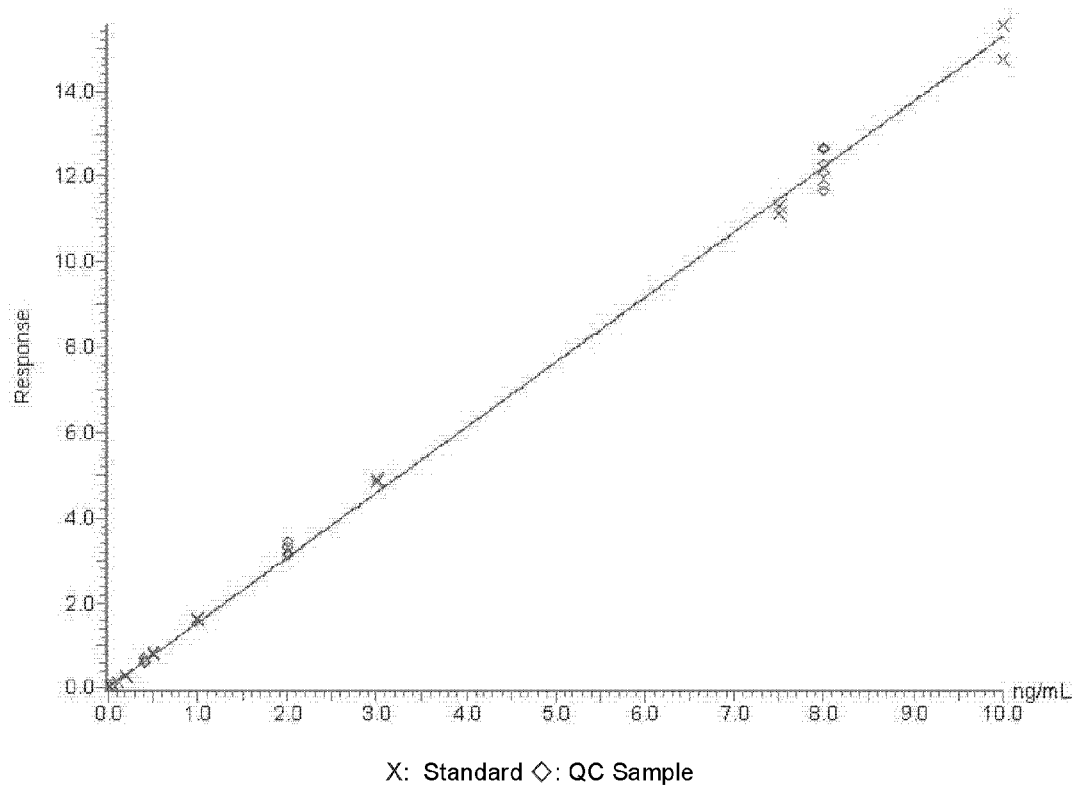
Figure 14  Representative LC/MS/MS Assay Calibration Standard Curve for Quantitation of N-Acetyl Amantadine in Incubation Samples

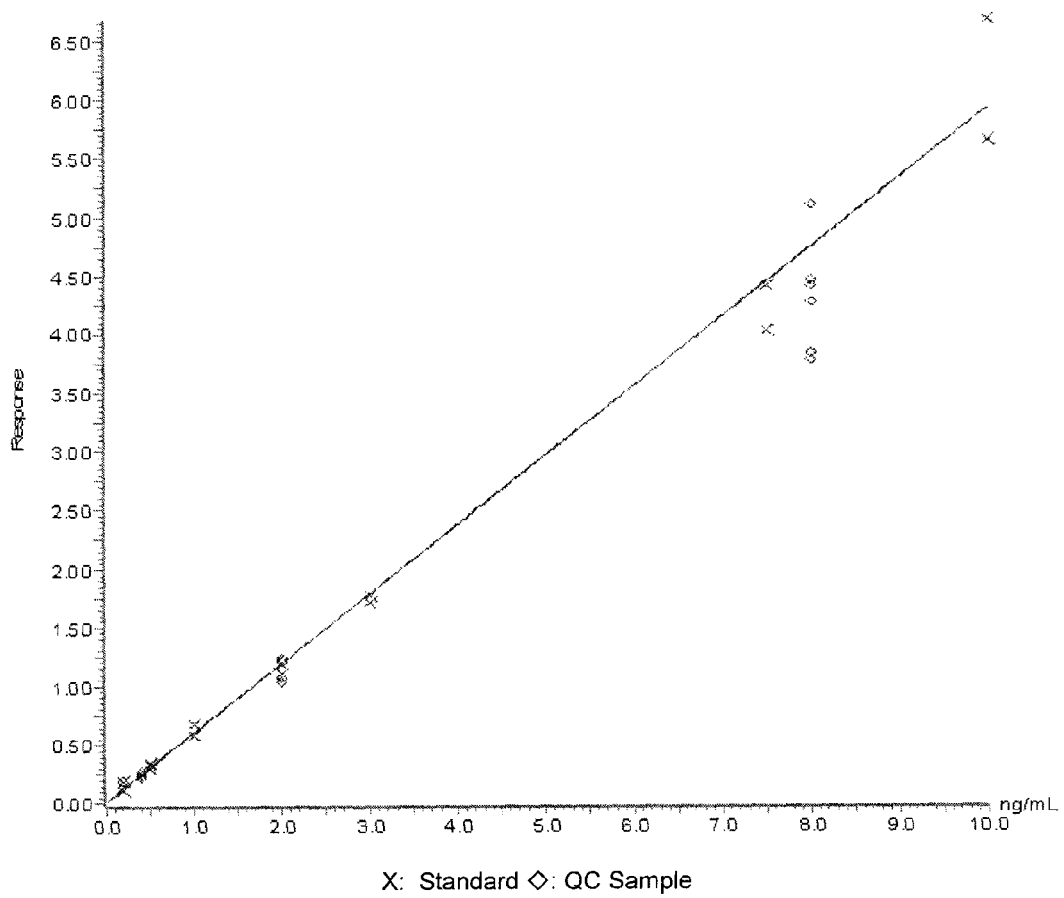
Figure 15    Representative LC/MS/MS Assay Calibration Standard Curve for Quantitation of N-Acetyl Rimantadine in Incubation Samples

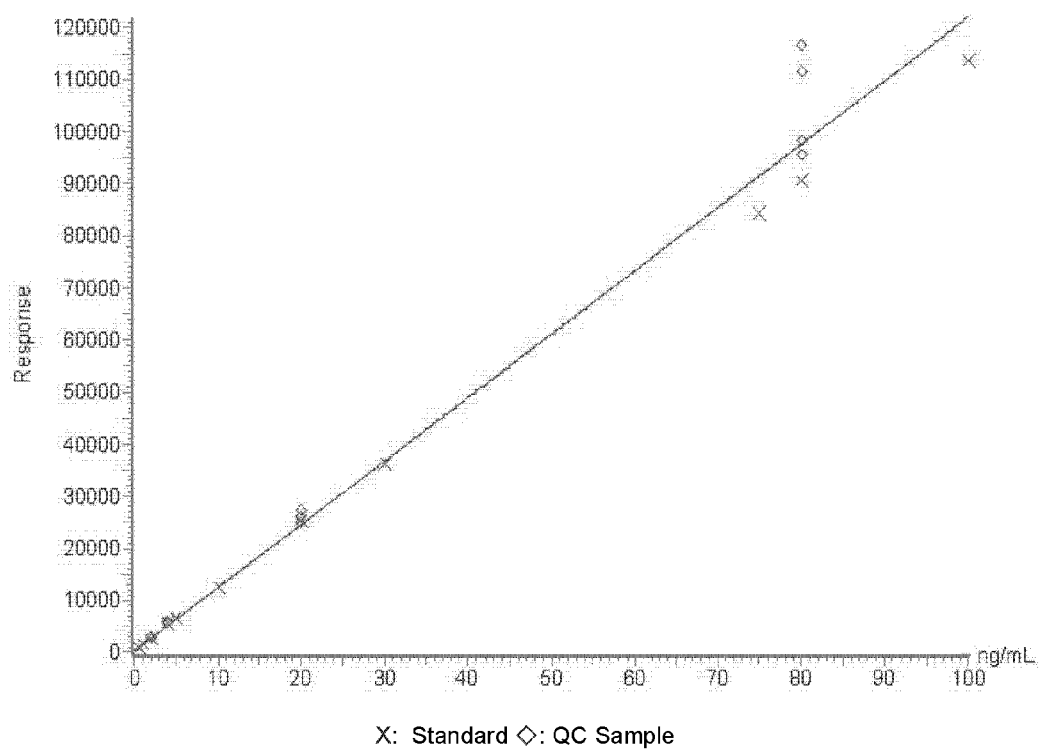
Figure 16  Representative LC/MS/MS Assay Calibration Standard Curve for Quantitation of N-Acetyl Tocainide in Incubation Samples

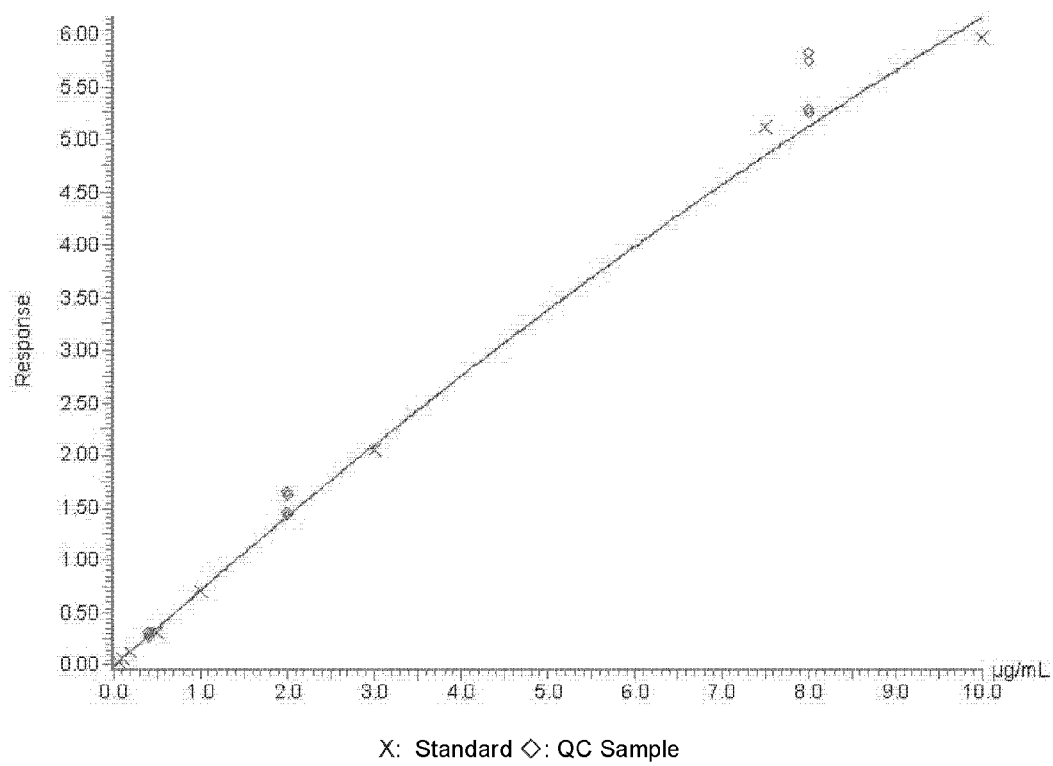
Figure 17  Representative LC/MS/MS Assay Calibration Standard Curve for Quantitation of N-Acetyl Spermidine in Incubation Samples

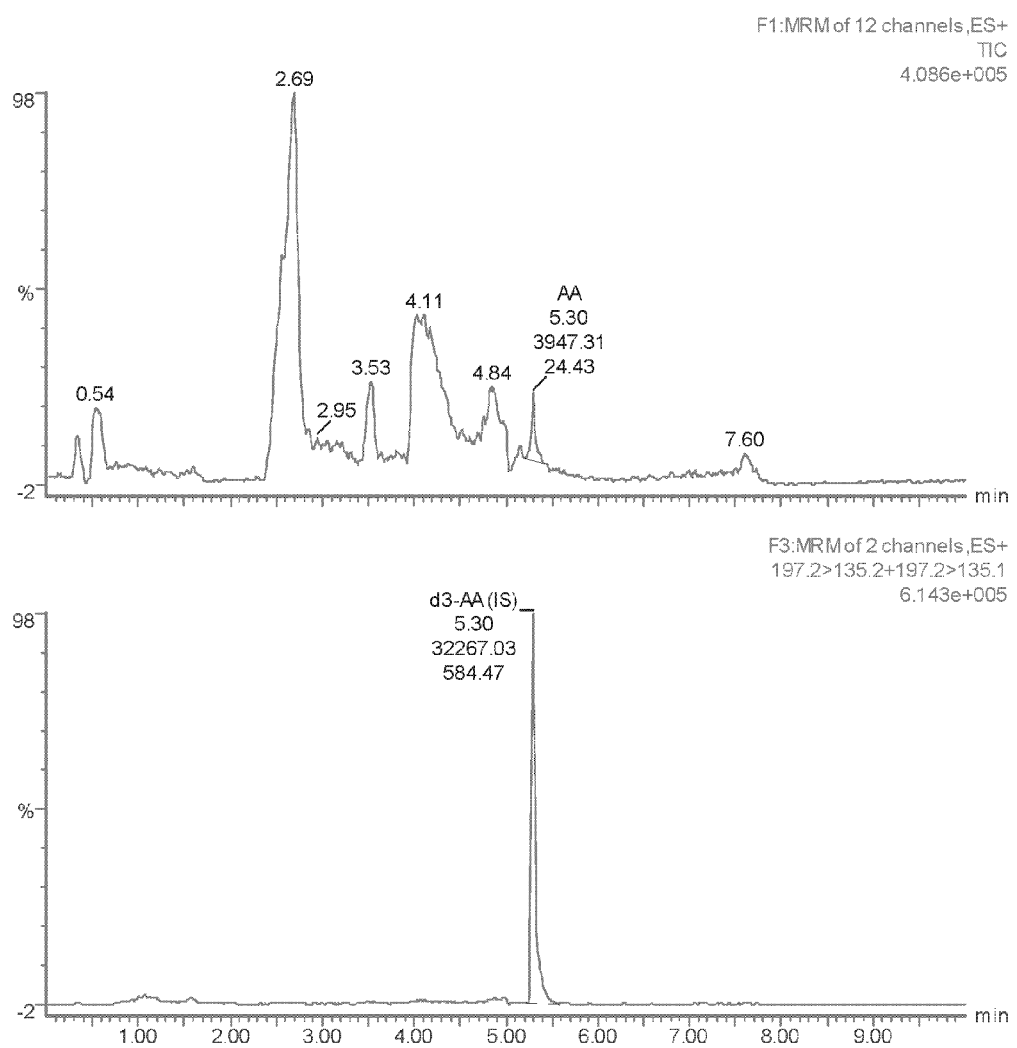
(Top: Chromatogram of N-Acetyl Amantadine; Bottom: Chromatogram of IS)
Figure 18  Representative LC/MS/MS Chromatogram of N-Acetyl Amantadine in Incubation Sample

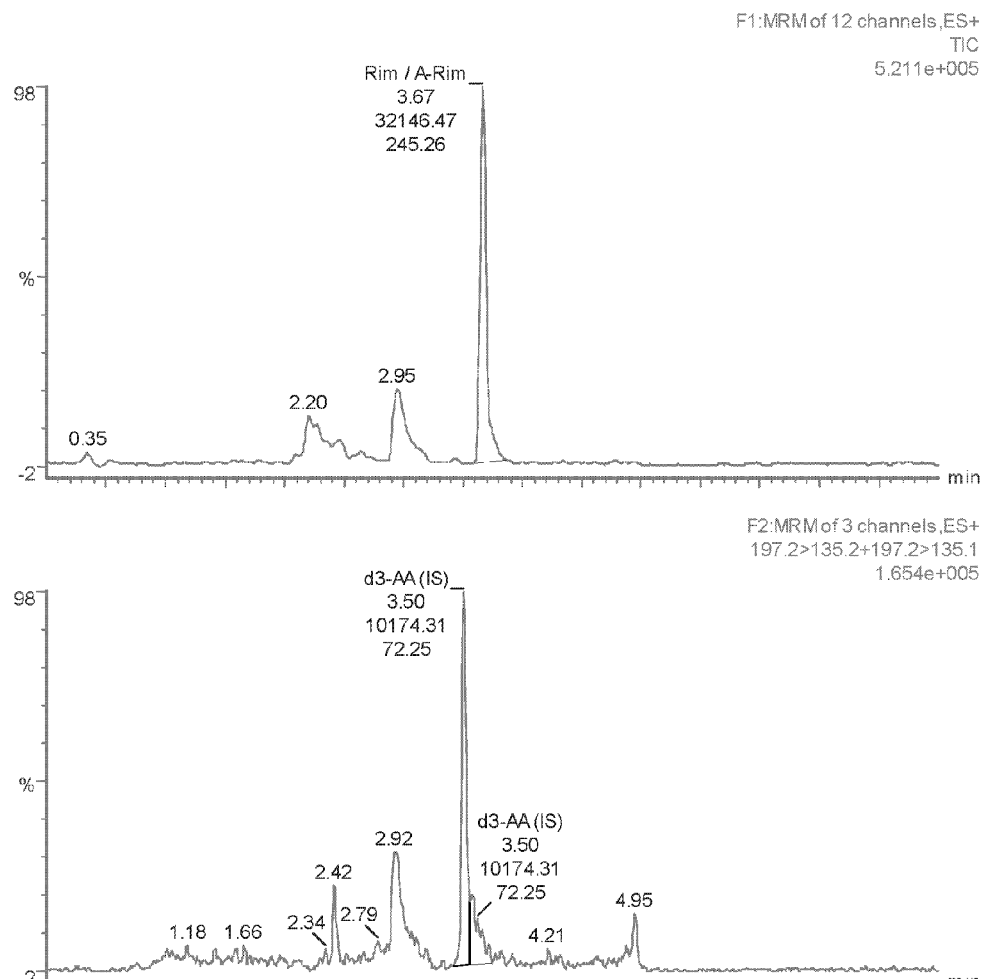
(Top: Chromatogram of N-Acetyl Rimantadine; Bottom: Chromatogram of IS)
Figure 19 Representative LC/MS/MS Chromatogram of N-Acetyl Rimantadine in Incubation Sample

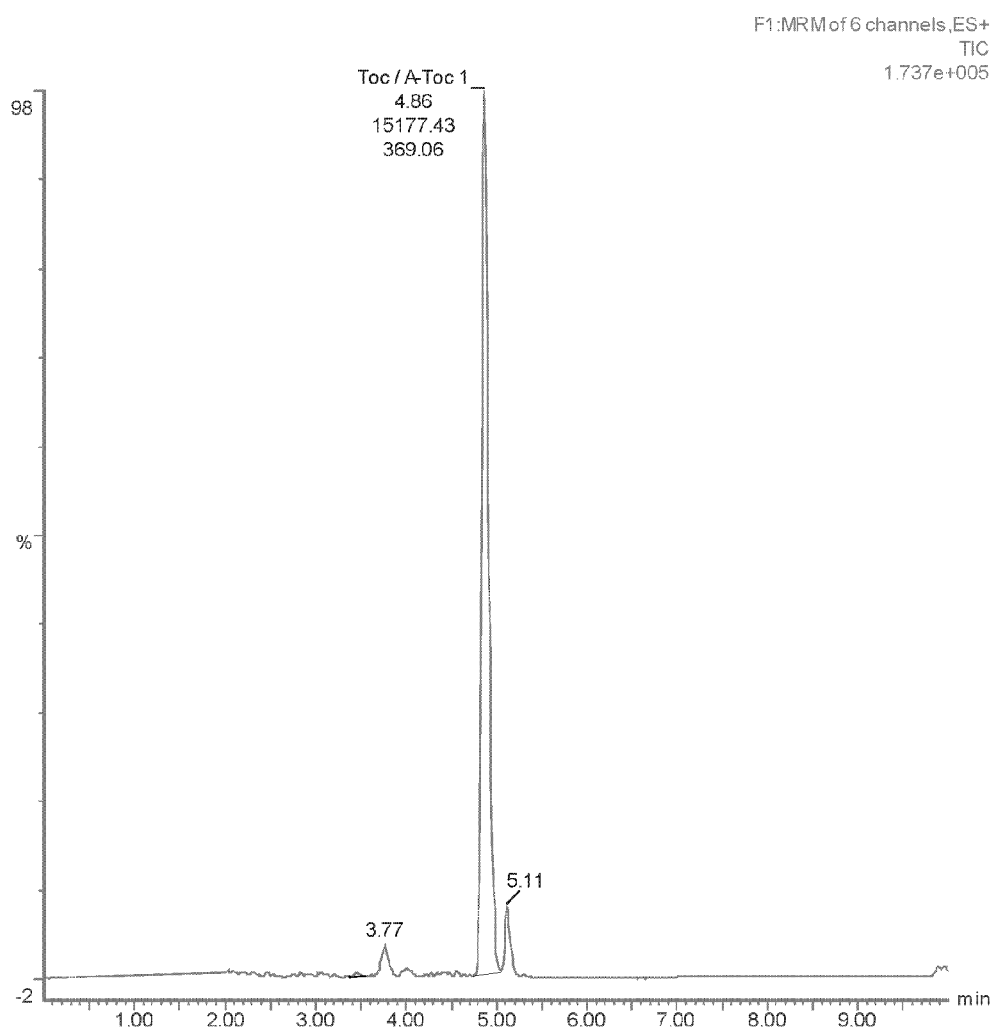
Figure 20  Representative LC/MS/MS Chromatogram of N-Acetyl Tocainide in Incubation Sample

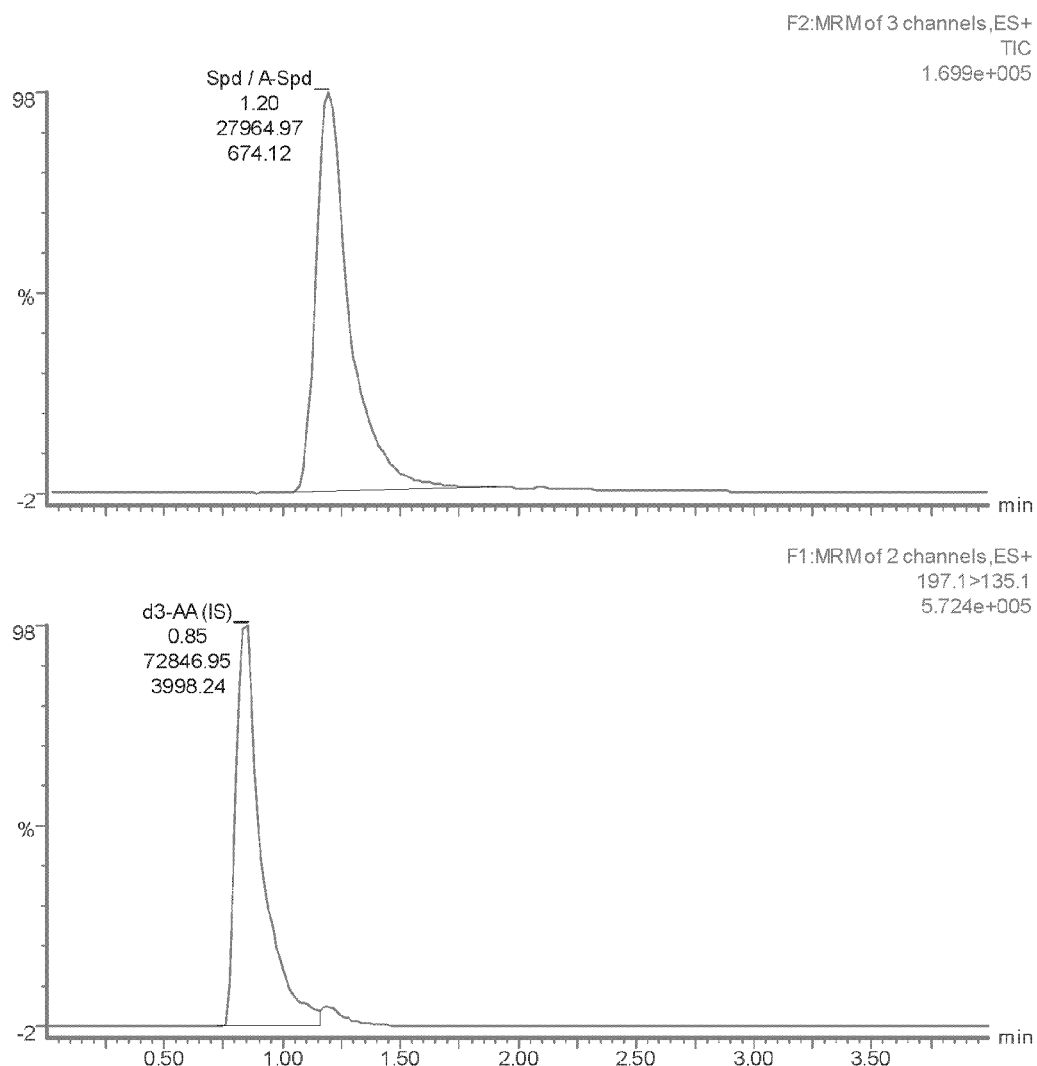
(Top: Chromatogram of N-Acetyl Spermidine; Bottom: Chromatogram of IS)
Figure 21  Representative LC/MS/MS Chromatogram of N-Acetyl Spermidine in Incubation Sample

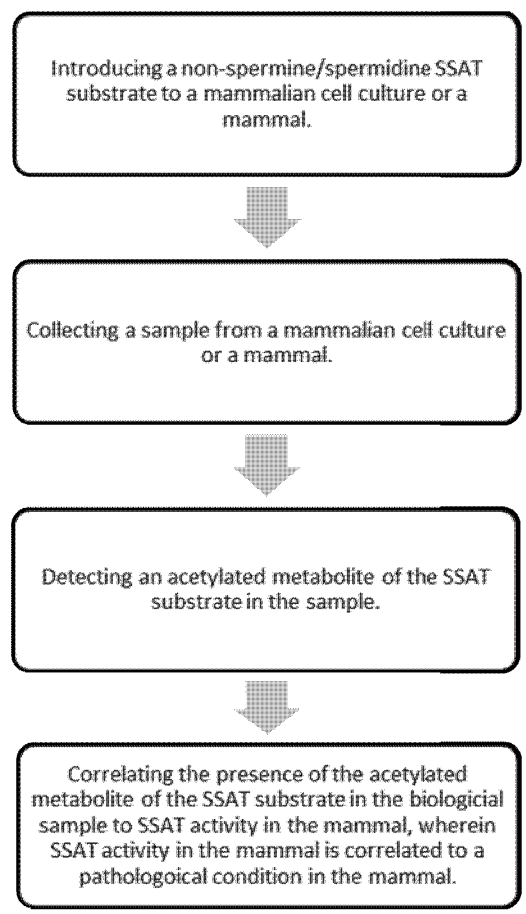
Figure 22    Method of Diagnosis using Assay

METHOD FOR ASSAYING THE ACTIVITY OF SPERMIDINE/SPERMINE $N^1$-ACETYLTRANSFERASE

CROSS-REFERENCE TO RELATED APPLICATION

This application is a continuation of and claims priority to U.S. patent application Ser. No. 14/358,695 filed May 15, 2014 entitled Method For Assaying The Activity Of Spermidine/Spermine $N^1$-Acetyltransferase, which is the U.S. National Phase of and claims priority to International Application No. PCT/CA2012/050828 filed Nov. 16, 2012 entitled Method For Assaying The Activity Of Spermidine/Spermine $N^1$-Acetyltransferase, which claims benefit of provisional application 61/560,700 filed in the United States Patent and Trademark Office on Nov. 16, 2012, all of which are incorporated herein by reference in their entireties.

BACKGROUND OF THE INVENTION

Field of the Invention

U.S. Pat. No. 6,811,967 which issued to Sitar et al. on Nov. 4, 2004, and the full disclosure of which is incorporated herein by reference, discloses a method for assaying activity of the enzyme spermidine/spermine $N^1$-acetyltransferase (SSAT) using SSAT substrates by detecting acetylated forms of the SSAT substrates. The SSAT substrates may include amantadine wherein metabolism of amantadine occurs in part by the action of the inducible enzyme SSAT to produce the acetylated metabolite N-acetylamantadine. Disclosed also is the correlation of SSAT activity to pathological conditions.

SSAT is ubiquitously distributed in mammalian tissues and plays a role in catabolism and elimination of polyamines from cells. SSAT is an inducible enzyme that catalyzes the transfer of an acetyl group from an acetylcoenzyme A to the aminopropyl moiety of the polyamines. This action by SSAT facilitates polyamine degradation, excretion, and cycling and/or intracellular cycling. In this manner SSAT participates in the maintenance of polyamine homeostasis in mammalian cells. However, in normal or uninduced mammalian tissues SSAT is present at very low levels.

Induction of SSAT expression can be caused by different drugs, growth factors, polyamines, polyamine analogues, toxic substances, hormones and physiological stimuli. Although all of the aforementioned compounds could cause induction of SSAT expression, induction occurs at different times for each individual compound. The regulation of SSAT expression occurs at the levels of transcription, mRNA stability, mRNA translation and protein stability. Induction or over-expression of SSAT is usually required for there to be sufficient SSAT enzyme present in cells or 100,000×g supernatant before in-vitro experiments can be successfully undertaken.

While current literature teaches that SSAT is an acetylating enzyme specifically for substrates including spermine and spermidine or its analogues, SSAT activity, SSAT enzyme kinetics and assay methodology for non-spermine/spermidine substrates of SSAT has not been understood. Current methods exist to quantify SSAT activity. However these techniques are dependent on highly skilled personnel and complicated experimental methods. More specifically, there has been a need for assay methodology which quantifies the activity of SSAT through detection of acetylated forms of non-spermine/spermidine substrates of SSAT that may be used to detect various pathological conditions.

SUMMARY OF THE INVENTION

There is provided a method for determining the activity of spermine/spermidine $N^1$-acetyltransferase (SSAT) in a mammal comprising the step of assaying a sample derived from the mammal for the level of an acetylated form of a non-spermine/spermidine, or analogues thereof, SSAT substrate in the sample.

In a first embodiment of the method the SSAT substrate is rimantadine and the acetylated form of the SSAT substrate is acetyl-rimantadine. The method may include incubating the SSAT substrate with mammalian tissue or cells at a specific SSAT substrate dosage level in the range of 1-10 mg/kg or, alternatively, at 3-6 mg/kg. Samples to be assayed may be urine, blood and/or saliva samples from the mammal, which may be collected at 2-24 hours following substrate incubation and, alternatively, at 2-4 hours following incubation.

In a second embodiment of the method the SSAT substrate is tocainide and the acetylated form of an SSAT substrate is acetyl-tocainide. The method may include incubating the SSAT substrate with mammalian tissue or cells at a specific SSAT substrate dosage level in the range of 1-10 mg/kg or, alternatively, at 3-6 mg/kg. Samples to be assayed may be urine, blood and/or saliva samples from the mammal which may be collected at 2-24 hours following substrate incubation and, alternatively, at 2-4 hours following incubation.

In a third embodiment of the method, SSAT activity is detected in hepatocytes and the method comprises the steps of:
a. obtaining a hepatocyte and incubating the hepatocyte in a suitable culture; and
b. incubating the hepatocyte with an non-spermine/spermidine SSAT substrate;
c. detecting an acetylated metabolite in a sample obtained from the culture; and
d. correlating the presence of the acetylated metabolite to SSAT activity, wherein the presence of the acetylated metabolite in the sample is indicative of SSAT activity in a mammal.

The drug may be rimantadine present in the range of 0-220 µM. The step of correlating the presence of the acetylated metabolite in the sample comprises correlating the amount of acetylated metabolite to a standard curve to determine the level of SSAT activity in the mammal.

In a fourth embodiment of the method, SSAT activity is assayed in mammal cells. The SSAT substrate is rimantadine and the acetylated form of the SSAT substrate is acetylated-rimantadine. The method comprises the steps of:
a. contacting a test sample obtained from the cell culture with a rimantadine;
b. measuring the amount of the acetylated metabolite produced; and
c. correlating the amount of an acetylated metabolite produced to a level of SSAT activity.

The cell culture may be a mammal cell culture and the test sample may be a hepatocyte. The step of contacting the test sample obtained from the cell culture with the drug may include incubating the sample with the substrate for about 24 hours.

In a fifth embodiment of the method, SSAT activity is detected in a mammal. The method comprises the steps of:
a. introducing rimantadine to the mammals
b. collecting biological fluids samples from the mammals c. detecting an acetylated metabolite in the samples; and d. correlating the presence of acetylated metabolite to SSAT activity, wherein the presence of the acetylated metabolite in the samples 1s an indicative of SSAT activity in the mammal.

The biological fluids may be, but are not limited to, blood, saliva and urine.

In a sixth embodiment of the method, SSAT activity is detected in a mammal. The method comprises the steps of:

a. introducing rimantadine to the mammals b. collecting a biological fluids sample from the mammals c. detecting an acetylated metabolite in the sample; and d. correlating the presence of acetylated metabolite to SSAT activity, where in the presence of the acetylated metabolite level in the sample is an indicative of cancer cells in the mammal.

The biological fluids may be, but are not limited, to blood, saliva and urine.

In embodiments of the method, the relative level of the non-spermine/spermidine substrate in the sample may be correlated to a standard curve representing known activity levels and may be assayed by a variety of techniques including but not limited to gas chromatography, radio-labelling, high pressure liquid chromatography (HPLC), thin layer chromatography; mass spectroscopy may be coupled with chromatography and affinity chromatography with specific antibody or antibodies.

The assay method disclosed herein may be used to correlate SSAT activity to a pathological condition in the mammal including but not limited to lung cancer, gastric carcinoma, ovarian cancer, acute myelocytic leukemia, lymphoma, breast cancer, renal cancer, colorectal cancer and/or prostate cancer.

BRIEF DESCRIPTIONS OF DRAWINGS

The invention will be more readily understood from the following description of the embodiments thereof given, by way of example only, with reference to the accompanying Figures, in which:

FIG. 1 is a table which shows the parameters (Km and Vmax) of the SSAT-mediated N-acetylation of amantadine, rimantadine, tocainide and spermidine in plateable cryopreserved primary rat hepatocytes;

FIG. 2 is a table which shows the enzyme kinetic data of amantadine N-acetylation by SSAT;

FIG. 3 is a table which shows the enzyme kinetic data of rimantadine N-acetylation by SSAT;

FIG. 4 is a table which shows the enzyme kinetic data of tocainide N-acetylation by SSAT;

FIG. 5 is a table which shows the enzyme kinetic data of spermidine N-acetylation by SSAT;

FIG. 6 is a table which shows on (dimethy]-2-thiazolyl)-2,5-diphenyl-2H-tetrazolium bromide or MTT assays from a pilot experiment;

FIG. 7 is a table which shows MTT assay results from a confirmatory experiment;

FIG. 8 shows metabolite formation and a Lineweaver-Burk Plot of N-acetylation of amantadine by SSAT;

FIG. 9 shows metabolite formation and a Lineweaver-Burk Plot of N-acetylation of rimantadine by SSAT;

FIG. 10 shows metabolite formation and a Lineweaver-Burk Plot of N-acetylation of tocainide by SSAT;

FIG. 11 shows metabolite formation and a Lineweaver-Burk Plot of N-acetylation of spermidine by SSAT;

FIG. 12 shows the results of an MTT assay from the pilot experiment;

FIG. 13 shows the results of an MTT assay from the confirmatory experiment;

FIG. 14 shows a representative LC/MS/MS assay calibration standard curve for the quantitation of N-acetyl amantadine in incubation samples;

FIG. 15 shows a representative LC/MS/MS assay calibration standard curve for the quantitation of N-acetyl rimantadine in incubation samples;

FIG. 16 shows a representative LC/MS/MS assay calibration standard curve for the quantitation of N-acetyl tocainide in incubation samples;

FIG. 17 shows a representative LC/MS/MS assay calibration standard curve for the quantitation of N-acetyl spermidine in incubation samples;

FIG. 18 shows a representative LC/MS/MS chromatogram of N-acetyl amantadine in incubation samples;

FIG. 19 shows a representative LC/MS/MS chromatogram of N-acetyl rimantadine in incubation samples;

FIG. 20 shows a representative LC/MS/MS chromatogram of N-acetyl tocainide in incubation samples;

FIG. 21 shows a representative LC/MS/MS chromatogram of N-acetyl spermidine in incubation samples; and FIG. 22 is a flow chart which shows a diagnostic method using a method for assaying SSAT as disclosed herein.

DESCRIPTIONS OF THE PREFERRED EMBODIMENTS

A method for assaying spermidine/spermine $N^1$-acetyltransferase (SSAT) activity in vitro and in vivo models is described herein.

SSAT is an important enzyme in polyamine metabolism. SSAT is highly regulated and its role in regulating neoplastic growth, obesity, stress response and oxygen homeostasis has been proposed. SSAT utilizes $N^1$-acetylspermine as a substrate in forming $N^1$, $N^{12}$-diacetylspermine. In vivo, SSAT is a cytosolic enzyme and $N^1$-acetylspermine is the preferred substrate compared with spermine, although the Km value for spermine is actually lower than that for $N^1$-acetylspermine. In addition to SSAT, arylamine N-acetyltransferases (NATs) are also cytosolic enzymes important in the N-acetylation of drugs and xenobiotics containing aromatic amine and hydrazine groups. In humans, two functional NAT isoforms (NAT1 and NAT2) and over 25 alleles of the two NAT isoforms have been identified.

In vitro and in vivo assays for evaluating SSAT activity based on liver homogenate derived from CD2F1 transgenic mice over-expressing SSAT have been published. Likewise, in vitro assays of NAT1 and NAT2 activities have also been described based on the use of human liver cytosol and human recombinant NAT1 and NAT2 isozymes. In both in vitro SSAT and NAT assays, acetyl-coenzyme A (co-factor) is required to provide activated acetyl group acetylation activity.

Rat and human primary hepatocytes in vitro assays have also been described in studies on SSAT and NAT activities. Since intact primary hepatocytes possess all of the required native drug metabolism co-factors, the use of an intact primary hepatocyte assay often offers a higher level of in vitro versus in vivo correlation of drug metabolism compared with alternative in vitro models based on microsome or subcellular cytosolic enzyme fractions.

Cytopreserved Primary Rat Hepatocytes

The following plateable primary cryopreserved rat hepatocytes were used in this study:

Identity: Cryopreserved Female Sprague-Dawley Rat Hepatocyte
BRIVAL Reference No: STM-1351 (TSY)
Supplier: Celsis
Lot No.: ASM
Identity: Cryopreserved Female Sprague-Dawley Rat Hepatocyte
BRIVAL Reference No: STM-1352 (TSY) and STM-1407 (TSY)
Supplier: Celsis
Lot No.: SKN Both lots were used in the pilot experiment. The confirmatory experiment was performed only with lot SKN.

Experimental Procedures

A pilot experiment was initially performed to screen for the suitable testing ranges of substrate concentrations, and to determine the concentrations that would result in significant cytotoxicity (relative viability <50%). Based on these preliminary results, a confirmatory experiment was performed with the adjusted substrate concentrations. Data generated from substrate concentrations that resulted in significant cytotoxicity were excluded from enzyme kinetic analysis. Refer to the table below for the testing concentrations. Metabolites collected from the incubation reactions were measured by LC/MS/MS analysis.

| Substrate | Experiment | Testing Concentrations ($\mu M$) |
|---|---|---|
| Amantadine | Pilot | 0, 53.4, 106.8, 186.9, 267, 400.5, 5354, 801, 1068, 1602, 2136 |
| | Confirmatory | 0, 106.8, 160.2, 213.6, 267, 400.5, 534, 667.5, 801, 934.5, 1068, 1335 |
| Rimantadine | Pilot | 0, 20, 40, 100, 200, 400, 600, 800 |
| | Confirmatory | 0, 20, 40, 60, 80, 100, 120, 150, 180, 200, 250, 300 |
| Tocainide | Pilot | 0, 10, 20, 50, 100, 200, 300, 400 |
| | Confirmatory | 0, 20, 40, 60, 80, 100, 150, 200, 300, 400, 500, 600, 800, 1000 |
| Spermidine[1] | Confirmatory | 0, 11, 22, 33, 55, 110, 165, 220, 275, 330, 440, 550 |

[1]Not tested in pilot experiment.

In general, the experimental procedures for the pilot and the confirmatory experiments were the same.

Preparation of Substrate Solutions

The substrates were accurately weighed, dissolved and further diluted with the appropriate solvent (10% dimethyl sulfoxide in distilled water (pilot) or 100% dimethyl sulfoxide (confirmatory) for tocainide; and deionized water for amantadine, rimantadine and spermidine) into a series of solutions at 100× of their testing concentrations outlined in the table above.

Preparation of Rat Hepatocytes

Both lots of female rat hepatocytes (Lots ASM and SKN; corresponding to BRIVAL ID: STM-1351 (TSY) and STM-1352 (TSY), respectively) were used in the pilot experiment. The confirmatory experiment was performed with lot SKN only (corresponding to BRIVAL ID: STM-1407 (TSY)). The preparation procedures outlined below were performed for both the pilot and the confirmatory experiments.

Immediately before use, cryopreserved primary rat hepatocytes were thawed in a water bath at 37° C. and resuspended in pre-warmed InVitroGRO™ CP Rat Medium. The viability of hepatocytes was confirmed to be above 70% based on Trypan Blue exclusion. Hepatocyte concentrations were adjusted by addition with InVitroGRO™ CP Rat Medium to achieve the target plating concentration of 0.70× $10^6$ cells/mL. Aliquots of hepatocytes were plated (0.5 mL/well) in 24-well CellAffix culture plates and the plates were placed in an incubator maintained at 37° C. with a highly humidified atmosphere of 95% air and 5% carbon for 4 hours to allow hepatocyte attachment before dosing with the selective substrate solutions.

Treatment and Incubation

Following cell attachment, the culture medium was aspirated from each well, and replaced with pre-warmed InVitroGRO™ HI Rat Medium (added with Torpedo antibiotic mix in the confirmatory experiment) and the substrate solution at the appropriate concentration. The treated cells were returned to incubation for 24 hours. Upon completion of incubation, the medium from each well was collected into 1.7-mL vials containing ice-cold methanol and stored at nominal −80° C. (−72° C. to −88° C.) prior to LC/MS/MS analysis. Hepatocytes remaining in the wells were subjected to MTT assay to evaluate the cytotoxic potential of the substrates at the testing concentrations.

MITT Cytotoxicity Assay

Upon collection of the reaction medium, an aliquot of 0.5 mg/mL MTT in KHB was added immediately to the remaining hepatocytes in each well and then incubated for approximately 30 minutes. Following incubation, the medium was replaced with dimethyl sulfoxide (DMSO) to dissolve the formazan. An aliquot from each well was measured for absorbance at 540 nm on a 96-well flat bottom plate with a microplate reader and DMSO for background absorbance correction.

Stability Control

Stability controls were tested to monitor any nonenzymatic N-acetylation of the substrates under the experimental conditions employed. In parallel to the hepatocyte samples, a set of stability controls consisting of only the substrate solutions at the testing concentrations in the InVitroGRO™ HI Rat Medium without hepatocytes was incubated for 24 hours under the same conditions as the hepatocyte samples. Upon completion of incubation, stability control samples were collected for LC/MS/MS analysis following the same procedures for the hepatocyte samples.

LC/MS/MS Analysis

Four LC/MS/MS assays were employed to individually quantitate the four metabolites in the incubation samples.

Refer to the table below for the reference standard used for the assay of each metabolite. Reference standard stock solutions were used for the preparation of calibration standards and quality control samples.

| Metabolite | Assay Reference Standard* |
|---|---|
| N-acetyl amantadine | N-acetyl amantadine |
| N-acetyl rimantadine | Rimantadine |
| N-acetyl tocainide | Tocainide |
| N-acetyl spermidine | Spermidine |

*Reference standards of some of the metabolites are not commercially available; hence, their corresponding substrates were used as the reference standards to calibrate for the assay of the metabolites in the incubation samples.

Deuterated N-acetyl-d, amantadine was added as an internal standard for all the assays.

In general, assays of the different metabolites shared the same sample preparation procedures described below:

Calibration Standards and Quality Control Samples:

The reference standard stock solution was diluted and added with aliquots of an assay matrix of methanol to blank incubation reaction buffer (1:1 v/v) and the internal standard to afford a series of calibration standards and quality control samples for LC/MS/MS analysis.

Incubation Samples:

The supernatant of each thawed incubation sample was added with an aliquot of the assay matrix and an aliquot of the internal standard prior to LC/MS/MS analysis.

Exceptions:

Thawed incubation samples for assays of N-acetyl tocainide and N-acetyl spermidine were acidified with formic acid (final formic acid at 0.5% v/v) prior to further preparation as described above. In addition, an acidified assay matrix was used for preparations of calibration standards, quality control samples, and incubation samples. This was to minimize potential metabolite binding to the preparation containers.

Calibration standards, quality control samples and incubation samples for quantitation of N-acetyl spermidine were diluted 10× with 0.1% formic acid in $diH_2O$ prior to addition of the internal standard and LC/MS/MS analysis.

Analytical Instrument Parameters

N-Acetyl Amantadine, N-Acetyl Rimantadine, and N-Acetyl Tocainide
Instrument: Waters Acquity™ UPLC system and Micromass™ Ultima
Acquisition software: MassLynx v4.1
Mobile Phase A: 0.1% formic acid in $diH_2O$
Mobile Phase B: 0.1% formic acid in methanol
Column: Synergi™ 4 u Hydro-RP (BRIVAL ID: LC-270)
Injection volume: 10 µL
MS mode: ESI positive MRM mode N-Acetyl Spermidine
Instrument: Waters Acquity'™ UPLC system and Micromass™ Ultima
Acquisition software: MassLynx v4.1
Mobile Phase A: 5 mM ammonium formate and 0.1% formic acid in $diH_2O$
Mobile Phase B: 5 mM ammonium formate and 0.1% formic acid in ACN:$diH_2O$ (9:1 v/v)
Column: Kinex™ 2.64 HILIC (BRIVAL ID: LC-309)
Injection volume: 1 µl,
MS mode: ESI positive MRM mode Data Analysis Software MassLynx™ v4.1 and Microsoft Excel 2007 were used for data analysis.

Analytical Data

Analytical data were printed on hardcopy and processed according to BRIVAL Standard Operating Procedures. Electronic data backup was performed via BRIPHARM Windows Server 2008 following BRIVAL Standard Operating Procedures.

Data Archiving

All experimental raw data, related documentation, and the study report will be archived at BRIVAL's archives (103-8898 Heather Street, Vancouver, BC, Canada) following procedures described in BRIVAL Standard Operating Procedures for a period of at least five years.

Results and Discussion

A summary of the relative enzyme kinetic parameters (Km and Vmax) of the SSAT-mediated N-acetylation of amantadine, rimantadine, tocainide and spermidine in plateable cryopreserved primary rat hepatocytes is shown in FIG. 1. Enzyme kinetics was evaluated based on the enzymatic conversion of the substrate at a range of testing concentrations into their N-acetylated metabolites over a 24-hour incubation reaction time course. Metabolite formation from different testing substrate concentrations after incubation was measured by LC/MS/MS and the resulting data constructed into Lineweaver-Burk plots of the double reciprocal of reaction velocity against substrate concentrations to estimate the Km and Vmax values of SSAT-mediated N-acetylation of each substrate tested.

The Km value of spermidine acetylation estimated from the confirmatory experiment was 287 µM, which is comparable to the literature reference of 267±46 µM derived from SSAT in cytosolic liver fraction of transgenic mice. Vmax cannot be compared to the literature as the values were presented in different units. From all stability controls, only negligible amounts of N-acetyl metabolites were observed, indicating that non-enzymatic N-acetylation was generally absent under the experimental conditions employed.

Results for each of the substrates from the confirmatory experiments are summarized in FIGS. 2 to 5. Their plots of metabolite formation against substrate concentrations, as well as the corresponding Lineweaver-Burk plots, are shown in FIGS. 1 to 4. Spermidine acetylation was observed to have the lowest Km value and the highest Vmax value at 287 µM and 7.21 pmol/min/million cells, respectively. Therefore, among all substrates tested, it has the highest relative maximum reaction rate. The Km values for the other substrates tested, in the ascending order, were 1659 µM for amantadine; 1835 µM for rimantadine; and 5033 µM for tocainide. The Vmax values of the substrates tested, in the descending order (corresponding to descending order of relative maximum reaction rate), were 0.617 pmol/min/million cells for tocanide, 0.364 pmol/min/million cells for rimantadine, and 0.00197 pmol/min/million cells for amantadine.

The cytotoxic potential of the substrates to rat hepatocytes was evaluated by MTT cytotoxicity assays. The assays were performed in both the pilot and the confirmatory experiments. Results from the pilot experiments are summarized in FIGS. 6 and 12. Significant cytotoxicity (relative viability <50%) was observed following treatments with higher concentrations of amantadine and rimantadine. Substrate concentrations that resulted in extensive cytotoxicity were observed to be approximately 1170 µM for amantadine and 280 µM for rimantadine. No cytotoxicity was observed from tocainide. Based on these results, the testing concentrations were adjusted accordingly for the subsequent confirmatory experiments.

MIT assay results from the confirmatory experiment are presented in FIGS. 7 and 13. The substrate concentrations resulting in extensive cytotoxicity were observed to be approximately 1140 µM for amantadine and 220 µM for rimantadine, confirming the initial findings from the pilot experiment. No cytotoxicity was observed from tocainide and spermidine at the testing range. Data generated from substrate concentrations that resulted in significant cytotoxicity were excluded from enzyme kinetic analysis.

Results from all calibration standards and quality control samples met the general batch acceptance criteria as per BRIVAL SOP-GP-011 (v7.0) and SOP-QA-025 (v1.0), established in accordance with FDA Bioanalytical Method Validation Guidelines. See, for example, "Guidance for Industry: Bioanalytical Method Validation" U.S. Department of Health and Human Services, FDA, CDER and CVM, May 2001, the full disclosure of which is incorporated herein by reference. All assays were quantitated with an internal standard approach, except for N-acetyl tocainide which was quantitated without the use of the internal standard. Representative calibration curves and LC/MS/MS chromatograms are presented in FIG. 7 to FIG. 14.

The enzyme kinetic parameters (Km and Vmax) of spermidine/spermine N1-acetyltransferase (SSAT) to mediate N-acetylation of amantadine, rimantadine, tocainide and spermidine were characterized. Among the substrates tested, spermidine acetylation was observed to have the lowest Km value and the highest Vmax value at 287 µM and 7.21 pmol/min/million cells, respectively. Therefore, it has the highest relative maximum reaction rate. The Km values for the other substrates tested, in the ascending order, were 1659 µM for amantadine; 1835 M for rimantadine; and 5033 µM for tocainide. The Vmax values of the other substrates tested, in the descending order (corresponding to descending order of relative maximum reaction rate), were 0.617 pmol/min/million cells for tocainide, 0.364 pmol/min/million cells for rimantadine, and 0.00197 pmol/min/million cells for amantadine.

It is concluded that determining the activity of spermine/spermidine $N^1$-acetyltransferase (SSAT) in a mammal by assaying a sample derived from the mammal for the level of an acetylated form of a non-spermine/spermidine SSAT substrate in the sample may be used to correlate SSAT activity to a pathological condition in the mammal as shown in FIG. 22.

It will be understood by a person skilled in the art that many of the details provided above are by way of example only, and are not intended to limit the scope of the invention which is to be determined with reference to the following claims.

What is claimed is:

1. A method for determining activity of spermine/spermidine N1-acetyltransferase (SSAT) in a mammal, the method comprising:
    (a) providing a biological sample from the mammal obtained 2-24 hours following administration of a single dose of rimantadine; and;
    (b) quantifying the level of N-acetyl rimantadine in the biological sample, thereby determining SSAT activity in the mammal.

2. The method of claim 1, wherein the biological sample is obtained from the mammal 2-4 hours following administration of the single dose of rimantadine.

3. The method of claim 1, wherein the biological sample is blood.

4. The method of claim 1, wherein the biological sample is urine.

5. The method of claim 1, wherein the biological sample is saliva.

6. A method for determining activity of spermine/spermidine N1-acetyltransferase (SSAT) in a mammal, the method comprising:
    (a) administering a single dose of rimantadine to the mammal;
    (b) collecting a biological sample from the mammal 2-24 hours following the single dose rimantadine administration; and
    (c) quantifying the level of N-acetyl rimantadine in the biological sample, thereby determining SSAT activity in the mammal.

7. The method of claim 6, wherein the biological sample is collected from the mammal 2-4 hours following administration of the single dose of rimantadine.

8. The method of claim 6, wherein the biological sample is blood.

9. The method of claim 6, wherein the biological sample is urine.

10. The method of claim 6, wherein the biological sample is saliva.

* * * * *